United States Patent
Nygaard Espeland et al.

(10) Patent No.: US 12,193,634 B2
(45) Date of Patent: Jan. 14, 2025

(54) METHOD FOR REAL-TIME DETECTION OF OBJECTS, STRUCTURES OR PATTERNS IN A VIDEO, AN ASSOCIATED SYSTEM AND AN ASSOCIATED COMPUTER READABLE MEDIUM

(71) Applicant: AUGERE MEDICAL AS, Oslo (NO)

(72) Inventors: Håvard Nygaard Espeland, Oslo (NO); Michael Alexander Riegler, Oslo (NO)

(73) Assignee: AUGERE MEDICAL AS, Oslo (NO)

( * ) Notice: Subject to any disclaimer, the term of this patent is extended or adjusted under 35 U.S.C. 154(b) by 382 days.

(21) Appl. No.: 17/620,639

(22) PCT Filed: Jun. 21, 2020

(86) PCT No.: PCT/NO2020/050170
§ 371 (c)(1),
(2) Date: Dec. 17, 2021

(87) PCT Pub. No.: WO2020/256568
PCT Pub. Date: Dec. 24, 2020

(65) Prior Publication Data
US 2022/0296081 A1   Sep. 22, 2022

(30) Foreign Application Priority Data

Jun. 21, 2019  (NO) .................................... 20190783
Aug. 2, 2019   (EP) .................................... 19189842

(51) Int. Cl.
*A61B 1/00*       (2006.01)
*G06V 10/50*      (2022.01)
(Continued)

(52) U.S. Cl.
CPC .. *A61B 1/000094* (2022.02); *A61B 1/000096* (2022.02); *G06V 10/50* (2022.01);
(Continued)

(58) Field of Classification Search
CPC ........ A61B 1/000094; A61B 1/000096; G06V 10/56; G06V 20/46; G06V 10/82; G06V 10/50; G06V 2201/031
See application file for complete search history.

(56) References Cited

U.S. PATENT DOCUMENTS

| | | | |
|---|---|---|---|
| 8,652,102 B2 * | 2/2014 | Nitsan | A61M 3/0283 604/150 |
| 10,482,313 B2 * | 11/2019 | Murthy | G06V 20/698 |
| 10,861,151 B2 * | 12/2020 | Liang | G06T 7/12 |
| 10,929,669 B2 * | 2/2021 | Zur | A61B 1/000094 |
| 11,017,526 B2 * | 5/2021 | Angermann | G06V 10/776 |
| 2013/0011016 A1 | 1/2013 | Haas | |

(Continued)

FOREIGN PATENT DOCUMENTS

| | | |
|---|---|---|
| CN | 109 523 535 A | 3/2019 |
| WO | WO 2017/027475 | 2/2017 |
| WO | WO 2018/007139 | 1/2018 |

OTHER PUBLICATIONS

European Search Report for EP 19 18 9842, mailed Mar. 11, 2020, 9 pages.

(Continued)

*Primary Examiner* — Gregory M Desire
(74) *Attorney, Agent, or Firm* — COATS & BENNETT, PLLC

(57) ABSTRACT

This invention relates to methods and systems for the real-time detection of objects, structures and/or patterns in videos, such as anatomical structures and/or anatomical landmarks in endoscopic videos of a subject, e.g. endoscopic videos of the gastrointestinal tract (GI tract).

22 Claims, 5 Drawing Sheets

(51) Int. Cl.
   *G06V 10/56* (2022.01)
   *G06V 10/82* (2022.01)
   *G06V 20/40* (2022.01)

(52) U.S. Cl.
   CPC .............. *G06V 10/56* (2022.01); *G06V 10/82* (2022.01); *G06V 20/46* (2022.01); *G06V 2201/031* (2022.01)

(56) References Cited

U.S. PATENT DOCUMENTS

2015/0065803 A1 3/2015 Douglas
2018/0182092 A1 6/2018 Drozdzal et al.
2019/0069957 A1 3/2019 Barral et al.

OTHER PUBLICATIONS

Hoerter et al., "Artificial Intelligence and Polyp Detection," *Current Treatment Options in Gastroenterology*, Published online: Jan. 21, 2020, pp. 120-136.

International Search Report and Written Opinion for PCT/NO2020/050170, mailed Dec. 12, 2020, 22 pages.

Matthews, "Comparison of the Predicted and Observed Secondary Structure of T4 Phage Lysozyme," *Biochimica et Biophysica Acta*, vol. 405, Oct. 1975, pp. 442-451.

Qadir et al., "Improving Automatic Polyp Detection Using CNN by Exploiting Temporal Dependency in Colonoscopy Video," *IEEE Journal of Biomedical and Health Informatics*, vol. 24, No. 1, Jan. 2020, pp. 180-193.

Sato et al., "Three-dimensional multi-scale line filter for segmentation and visualization of curvilinear structures in medical images," *Medical Image Analysis*, vol. 2, No. 2, Feb. 1998, pp. 143-168.

Tan et al., "EfficientNet: Rethinking Model Scaling for Convolutional Neural Networks," *Proceedings of the 36th International Conference on Machine Learning*, Jun. 2019, 10 pages.

Van Rijn et al., "Polyp Miss Rate Determined by Tandem Colonoscopy: A Systematic Review," *American Journal of Gastroenterology*, © 2006, pp. 343-350.

Yu et al., "Integrating Online and Offline Three-Dimensional Deep Learning for Automated Polyp Detection in Colonoscopy Videos," *IEEE Journal of Biomedical and Health Informatics*, vol. 21, No. 1, Jan. 2017, pp. 65-75.

* cited by examiner

METHOD FOR REAL-TIME DETECTION OF OBJECTS, STRUCTURES OR PATTERNS IN A VIDEO, AN ASSOCIATED SYSTEM AND AN ASSOCIATED COMPUTER READABLE MEDIUM

CROSS REFERENCE TO RELATED APPLICATIONS

This is the U.S. National Stage of International Application No. PCT/NO2020/050170, filed Jun. 21, 2020, which was published in English under PCT Article 21 (2), which in turn claims the benefit of European Patent Application No. 19189842.8, filed on Aug. 2, 2019, which in turn claims the benefit of Norway application No. 20190783, filed on Jun. 21, 2019.

This invention relates to methods and systems for the real-time detection of objects, structures and/or patterns in videos, such as anatomical structures and/or anatomical landmarks in endoscopic videos of a subject, e.g. endoscopic videos of the gastrointestinal tract (GI tract).

The GI tract is an organ system within humans or other animals that extends from the mouth to the anus, forming a continuous passageway and comprising all structures and organs in between those two, e.g. the mouth, the esophagus, the stomach, the small intestines and the large intestines. Its function relates to intake and digestion of food, absorption of energy and nutrients and excretion of the remaining waste. The GI tract is divided into certain discrete regions, e.g. the upper and lower GI tract which in itself are divided into various discrete sub-regions. Anatomical landmarks are often used as a demarcation between the various regions and sub-regions, e.g. the pylorus connects the stomach to the duodenum while the cardia forms the connection of the esophagus to the stomach.

The innermost layer of tissue of the GI tract is the mucosa, which plays an important role since it comes in direct contact with the luminal contents of the GI tract, such as food and stool. If the GI tract is inspected endoscopically, it is the mucosa that becomes visible to the physician. The appearance of the mucosa is an important indication of the state of the health of the GI tract and alterations of the mucosa. Atypical texture and color, erosions, ulcerations, vascular malformations, inflammation, hemorrhages or polyps may be signs of a disease such as Barrett's esophagus, stomach ulcers, inflammatory bowel diseases (IBD), such as Crohn's disease or ulcerative colitis or colon cancer.

During endoscopy, the physician visually examines the interior surface of the GI tract using an endoscope, e.g. a colonoscope, a gastroscope or a duodenoscope, to visually identify alterations on such interior surface. Nowadays, an endoscope system generally includes a video camera, which acquires a video of the inspected interior surface, and a monitor where the video is displayed in real-time for the practitioner carrying out the procedure.

While some alterations of the interior surface of the GI tract may be relatively easy to detect, others are more challenging, which may be due to their size, appearance or location in the GI tract. For instance, only about 74-81% of the polyps are actually detected in a colonoscopy procedure, i.e. 19-26% are missed (J. C. van Rijn et al., Am. J. Gastroenterol., 101(2), 2006, 343-350). This figure is alarming since as of 2012, colorectal cancer is the second most common cause of cancer in women and the third most common in men. In 2018, 1.8 million people were diagnosed with colorectal cancer and 881 000 people died from it. As more than 80% of colorectal cancers arise from adenomatous polyps, detection and removal of such polyps is crucial for preventing them to turn into cancer. The high miss of polyps is due to many factors, including the fact that the interior of the colon has many curves and folds, poor quality of bowel preparation, size and shape/appearance of the polyps and skill of the physician performing the colonoscopy.

Several methods and systems have been proposed to improve the accuracy (i.e. reducing the rate of false positive or false negative results) of detecting polyps. Most of these relate to computer-aided detection of polyps in endoscopic images, i.e. are not suitable for real-time detection and display of the detected polyps together with the video feed from the colonoscopy.

WO 2017/027475 discloses a method for simultaneously monitoring colonoscopic video quality and detecting polyps in colonoscopy. The method includes the use of a first trained classifier that monitors image frames from a colonoscopic video to determine which image frames are informative frames and which image frames are non-informative frames and that passes the informative image frames to an automatic polyp detection system that uses a second trained classifier to localize and identify whether a polyp or any other object of interest is present in one or more of the informative image frames. The disadvantage of this method is that the first trained classifier cannot be "perfect", i.e. some of the frames that are classified as non-informative are in fact informative and are discarded. This error is carried over to the next step where the second classifier consequently will miss polyps that are present in the discarded frames.

WO 2018/007139 discloses a method for performing real-time detection and displaying of polyps in optical colonoscopy which includes selecting one single color channel per real-time image for obtaining single color pixels, extracting a plurality of single color pixels local features of the real-time image, using a classifier to determine if a polyp is present and real-time framing the position of the identified polyp on display. While this method is fast, the downside is that from the overall information present in the video frames, only that of a single color channel is used, i.e. valuable other information for the detection is not used.

US 2019/0069957 discloses a system and method for robotic surgery to recognize organs and other anatomical structures in the body (in real-time), while performing surgery. A machine learning model, e.g. a deep learning model, is trained to recognize anatomical structures within surgical videos. Once image classification has been learned by the algorithm, the system may use a sliding window approach to find the relevant structures (points of interest) in the images of videos obtained during surgery. The sliding window scans/slides across an image, and applies an image classifier in order to determine if the window includes an interesting object. The disadvantage of this method is that applying the sliding window to one and one image, the temporal correlation between the images is lost. As such, false positive detections will occur by wrong classifications of single frames, and conversely false negatives can occur when structures can only be classified correctly by using the context of multiple frames.

US 2018/0182092 discloses a system and method for a difference measure to identify points of change in an image stream captured in vivo during capsule endoscopy with the aim to provide a summarized representation of the image stream and thus reduce the physicians viewing time of said image stream. A set or window of sequential frames in the image stream is used to carry out the difference measure.

The disadvantage of this method is that by selecting a set of frames, only a part of the overall available information is used, i.e. a part of the information is discarded, which may be of importance for the identification of the points of change and such points of change may be missed.

L. Yu et al., IEEE J Biomed Health Inform 24 (1), 2017, 65-75, describe the use of three-dimensional deep learning for automated polyp detection in colonoscopy videos to exploit temporal information by simultaneous analysis of seven future and eight previous image frames of the video. While this method exploits the temporal information of a polyp, it requires extensive computational resources and with 1.23 seconds processing time per frame, the method is not suitable for real-time automated polyp detection.

H. A. Qadir et al., IEEE J Biomed Health Inform 24 (1), 2020, 180-193, describe a method to exploit temporal information to reduce false positives in automated polyp detection colonoscopy videos. In the method, regions of interest (ROIs) are extracted using a common object detector network and a filter is applied to previous/future video frames. The filter combines results of multiple ROIs assumed to be of the same polyp and verifies that the probability of a ROI being a polyp is high for multiple frames. Although this is a fast approach that can be used in real-time, it will lack the sensitivity obtained with the method by Yu: since a system implementing the method of Qadir is threshold based, a feature must first be detected in individual frames for the system to work. It cannot combine multiple images to enhance the detection of a feature. An analogy is that a human can see a polyp in a video sequence, but not when looking at isolated individual frames.

N. Hoerter et al., Curr Treat Options Gastro 18, 120-136, 2020 provide a review of the history, recent advances and ongoing challenges of artificial intelligence in colonic polyp detection. The authors report that as of today, only two studies have applied computer aided detection of polyps in vivo during a live colonoscopy, i.e. in real-time. In one study, the system used did not detect any additional polyps that were missed by the endoscopists, thus making the added value of the system questionable. In the other study, most of the adenomas detected were non-advanced and carried relatively low malignant potential. The system also detected a larger number of hyperplastic polyps, which could increase procedural time and risk of unnecessary resection.

Accordingly, there is a need for real-time detection of polyps and other anatomical structures in a video feed from an endoscopic video.

In a first aspect, the invention provides a method for real-time detection of one or more anatomical structures and/or one or more anatomical landmarks in an endoscopic video, the method comprising
  a) receiving a sequence of frames of the endoscopic video;
  b) applying a sliding window to the sequence of frames and for each position of the sliding window extracting one or more visual features from said frames within the sliding window, thereby generating a plurality of time images;
  c) applying a trained classifier to each time image, wherein the trained classifier determines one or more detection scores that indicate the likelihoods that the respective time image contains one or more of said anatomical structures and/or one or more of said anatomical landmarks; and
  d) outputting in real-time the detection of said one or more anatomical structures and/or said one or more anatomical landmarks when the detection score is higher than a detection threshold of the trained classifier.

The endoscopic video is generated during an endoscopic procedure. The endoscopic procedure may be one where the endoscope is inserted into a body orifice, e.g. an endoscopic procedure performed in the GI tract, such as capsule endoscopy esophagosgastroduodenoscopy, panendoscopy, gastroscopy, enteroscopy, anoproctosigmoidocolonoscopy, colonoscopy, sigmoidoscopy, rectoscopy, or in the respiratory tract, such as rhinoscopy or bronchoscopy, or a cystoscopy or falloposcopy. Alternatively, the endoscopic procedure is one where the endoscope is inserted into the body through a small incision, e.g. laparoscopy, cholangioscopy, arthroscopy, thoracoscopy or mediastinoscopy.

In one embodiment, the endoscopic video is generated during an endoscopic procedure performed in the GI tract. In another embodiment, the endoscopic video is generated during an endoscopic procedure performed in the colon and/or the rectum, i.e. during a colonoscopy, sigmoidoscopy or rectoscopy.

The method of the invention allows for the real-time detection of one or more anatomical structures and/or one or more anatomical landmarks. The method makes use of all the information present in the video frames without limiting it to a certain sub-set of information. This allows for a more reliable detection. By "condensing" the information present in a sequence of frames into a time image as done in step b), a data unit is generated whose processing requires less processing time compared to processing each frame separately and at the same time preserving the temporal correlation between the frames.

The method of the invention preferably detects one or more anatomical structures and/or one or more anatomical landmarks in real-time while the video is still being received. Nevertheless, it will be appreciated that while the detection is in real-time, it is not necessarily instantaneous and here may be processing and/or buffering delays, e.g. of a few milliseconds.

An anatomical structure in the context of this invention is a part or structure located on the inside of the human or animal body, which can be visualized by endoscopy. By way of example, in the GI tract, anatomical structures include the interior surface of the GI tract, including healthy mucosa, stool, fluids like gastric fluid or colonic fluid and blood vessels but also abnormal and/or diseased tissue or structures such as abnormal mucosa, e.g. inflamed mucosa, erosions, lesions (e.g. ulcers) or polyps. The anatomical structures include dyed structures, e.g. mucosa that has been dyed with a dye such as methylene blue. Methylene blue is a chemical that sprayed onto the mucosa of the GI tract in order to help identifying dysplasia or pre-cancerous lesions.

An anatomical landmark in the context of this invention is a region, part or structure located on the inside of the human or animal body which can be visualized by endoscopy and which forms a demarcation. As mentioned above, the GI tract is an organ system that extends from the mouth to the anus, forming a continuous passageway and comprising all structures and organs in between those two. Anatomical landmarks in the GI tract include the pylorus (which connects the stomach to the duodenum), the cardia (which forms the connection of the esophagus to the stomach), the cecum (which marks the beginning of the large intestine) and the z-line (which marks the beginning of the beginning of the gastric mucosa and can be seen as an irregular zig-zag line).

In one embodiment, the method of the invention allows for the real-time detection of one or more anatomical structures, e.g. polyps and stool. Practitioners who carry out a colonoscopy look for structures that are indicative of colonic polyps. Stool often appears like polyps in the video obtained from the colon during colonoscopy. Stool may also obscure polyps from the view of the practitioner. For example, stool can cover polyps partially or completely. As a result, stool may have a significant impact on the sensitivity with which practitioners detect polyps and hence there is a need for a tool like the method of the invention for the real-time detection of polyps and stool to help the practitioner to detect polyps and distinguish them from stool. In another embodiment, the method of the invention allows for the real-time detection of one or more anatomical landmarks, e.g. the z-line and the pylorus. Practitioners who carry out an esophagosgastroduodenoscopy (i.e. endoscopy of the upper GI tract) will hence receive real-time information on which segment of the upper GI tract they are looking at. In yet another embodiment, the method of the invention allows for the real-time detection of one or more anatomical structures and one or more anatomical landmarks, e.g. inflamed mucosa (i.e. redness of the mucosa) and the pylorus and the cecum. If such information is provided to the practitioner during capsule endoscopy, the practitioner will not only receive information that an inflammation is present but also the localization of said inflammation, i.e. in this case whether the inflammation occurs in the small intestine or the large intestine.

The methods of the invention can be implemented on a system for real-time detection of one or more anatomical structures and/or one or more anatomical landmarks in an endoscopic video.

Hence, in a second aspect the invention provides a system for real-time detection of one or more anatomical structures and/or one or more anatomical landmarks in an endoscopic video, said system comprises (i) an input configured to receive a sequence of frames of the endoscopic video, (ii) a processing system configured to access and process the sequence of frames and (iii) an output configured to output in real-time the detection of said one or more anatomical structures and/or one or more anatomical landmarks, wherein the processing system is configured to process the sequence of frames with the steps comprising:

a) receiving a sequence of frames of the endoscopic video;

b) applying a sliding window to the sequence of frames and for each position of the sliding window extracting one or more visual features from said frames within the sliding window, thereby generating a plurality of time images;

c) applying a trained classifier to each time image, wherein the trained classifier determines one or more detection scores that indicate the likelihoods that the respective time image contains one or more of said anatomical structures and/or one or more of said anatomical landmarks; and d) outputting in real-time the detection of said one or more anatomical structures and/or said one or more anatomical landmarks when the detection score is higher than a detection threshold of the trained classifier.

In a third aspect the invention provides a computer readable medium storing computer readable instructions for real-time detection of one or more anatomical structures and/or one or more anatomical landmarks in an endoscopic video, the computer program instructions when executed by a processing system perform operations comprising:

a) receiving a sequence of frames of the endoscopic video;

b) applying a sliding window to the sequence of frames and for each position of the sliding window extracting one or more visual features from said frames within the sliding window, thereby generating a plurality of time images;

c) applying a trained classifier to each time image, wherein the trained classifier determines one or more detection scores that indicate the likelihoods that the respective time image contains one or more of said anatomical structures and/or one or more of said anatomical landmarks; and d) outputting in real-time the detection of said one or more anatomical structures and/or said one or more anatomical landmarks when the detection score is higher than a detection threshold of the trained classifier.

In one embodiment, the computer readable medium is a non-transitory computer readable medium. In another embodiment, the computer readable medium is a transitory computer readable medium.

In a fourth aspect the invention provides an endoscope system comprising a system according to the invention and an endoscope connected to or in communication with the input of said system.

The method and system of the invention allows for the real-time detection of anatomical structures and/or landmarks of interest during an endoscopic procedure. In another embodiment, the method and system of the invention is used for the training and education of medical students, residents or health personnel in general.

The method of the invention has been explained in detail in the context of endoscopic videos of the GI tract but as mentioned herein, the method of the invention may be used for the detection of anatomical structures and/or landmarks of interest in other types of endoscopic videos. Thus, by way of example, the endoscopic video may be one generated during cystoscopy, i.e. the visual inspection of the inside of the bladder with a flexible or rigid endoscope (cystoscope) to identify abnormalities and diseases like bladder cancer.

Anatomical structures of interest are inflammation (cystitis), benign papillomas and papillary carcinomas, both finger-like projections from the inner surface of the bladder toward the hollow center or flat carcinomas.

Cystoscopy may be carried out with white light. However, the use of white light can lead to missing lesions that are present but not visible, especially flat carcinomas and aggressive carcinoma in situ. To improve detection, photosensitizing imaging agents can be used like Hexvix®, which comprises hexylaminolevulinate (HAL) or Vidon®, which comprises PVP-Hypericin. Such agents, when taken up into a cell, are converted into porphyrins, which are photosensitizers and fluorescent compounds. Under subsequent blue-light illumination from a blue light cystoscope, the porphyrins emit red light and thus enable specific and accurate visualization of e.g. a tumor. Thus, anatomical structures of interest also include "dyed", i.e. red-fluorescent inflamed bladder tissue or carcinomas.

Further, by way of example, the endoscopic video may be one generated during bronchoscopy, i.e. the visual inspection of the inside of the airways with a flexible or rigid endoscope (bronchoscope) to identify abnormalities and diseases like lung cancer or sarcoidosis.

Several embodiments of the present invention will now be described, by way of example only, with reference to the accompanying drawings in which:

FIG. 1 is a flowchart setting forth steps of a method in accordance with the present invention. In some embodiments, the method may be carried out using the system 400 as described with respect to FIG. 4.

Figure 1:
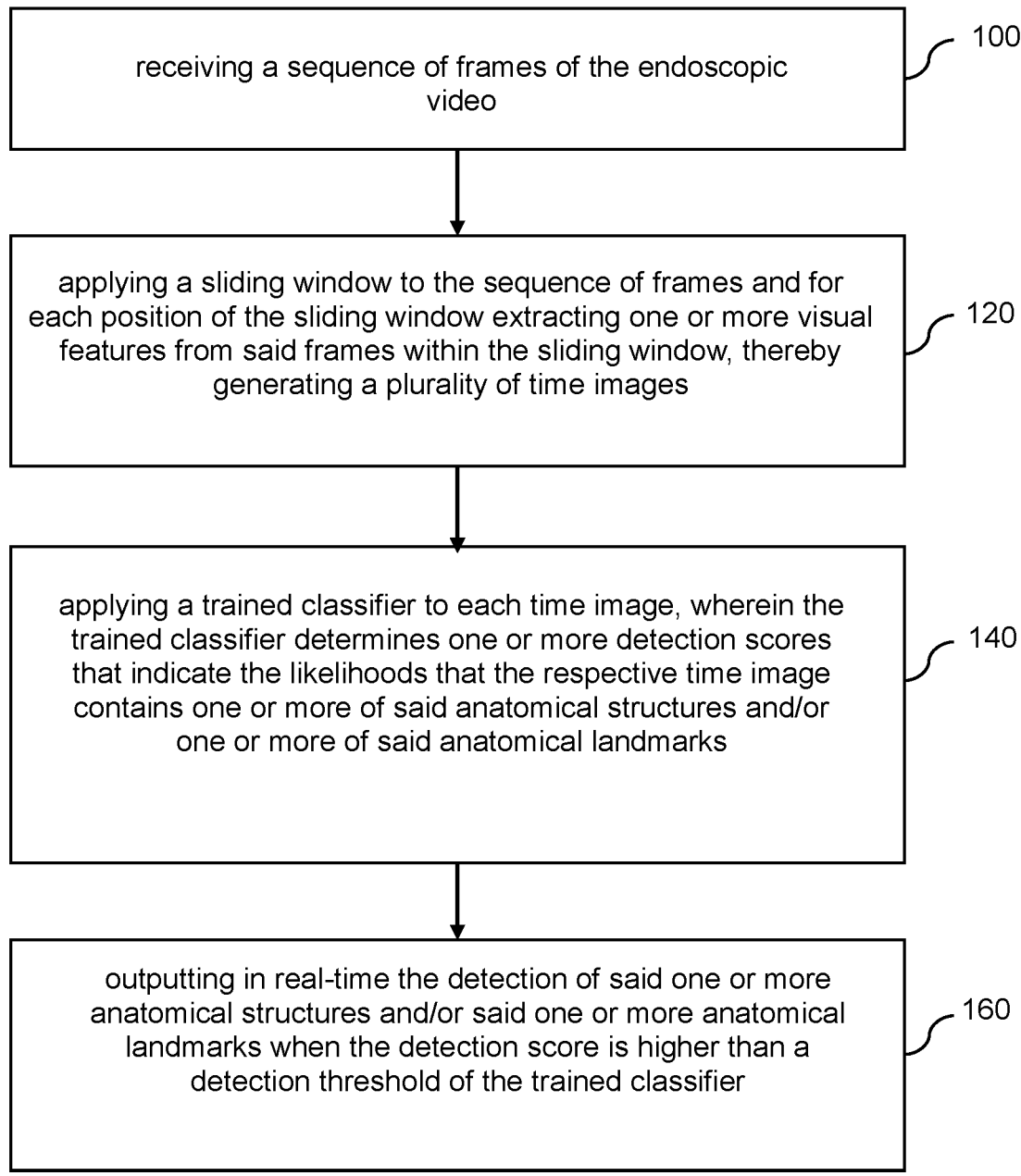
FIG. 1 is a flowchart setting forth steps of a method in accordance with aspects of the present invention.

At step 100, the method begins with receiving a sequence of frames of an endoscopic video. As described, the sequence of frames is received in real-time from a life video feed of the endoscopic procedure. The system of the invention is configured for real-time processing and preferably configured to receive and process at least about 24 frames per second, e.g. 24 frames/s. The viewer of the video (e.g. the practitioner) will typically perceive a frame rate of 24 frames/s as fluid motion. The term "sequence of frames" is meant to indicate that the frames are in the correct sequential order, i.e. correct temporal order.

At step 120, a sliding window is then applied to the sequence of frames and for each position of the sliding window; one or more visual features are extracted from said frames within the sliding window, thereby generating a plurality of time images. The resolution of a time image depends on the amount of data in said time image, i.e. a large amount of data results in a high resolution while a small amount of data results in a low resolution. The resolution of the time image affects processing time. With the method of the invention, a time image of at least 1024×768 pixel can be processed in real-time.

In one embodiment, the size of the sliding window is fixed, e.g. the sliding window includes 2, 3, 4, 5, 6 or more frames. The size of the sliding window affects the resolution of the time image generated for each position of the sliding window. For a given number of visual features, a smaller size sliding window, e.g. a sliding window that includes 2 or 3 frames, results in time images having a lower resolution than if the applied sliding window had a larger size, e.g. 5 or 6.

In another embodiment, the size of the sliding window is dynamic, i.e. its size varies. This may be useful to achieve a trade-off between resolution and processing time, e.g. when the region of the GI tract that is currently under examination is not of particular interest for polyp detection, but segmentation information is required by the practitioner. The system of the invention may apply a sliding window that results in a lower resolution of the time image, which is sufficient for segmentation, while for polyp detection in a segment of interest, the system may apply a sliding window that results in a higher resolution of the time image required for a reliable polyp detection.

The sliding window be an overlapping or a non-overlapping sliding window. A non-overlapping sliding window will include different frames for each of its positions, e.g. a non-overlapping sliding window including 5 frames will at its first position include frames 1 to 5, at its second position frames 6 to 10, at its third position frames 11 to 15 and so on. Another embodiment of non-overlapping sliding window is one that skips one or more frames. As an example, a sliding window may be applied which includes 5 frames and which skips each 6th frame, i.e. the first position of the sliding window is frame 1 to frame 5, the second position of the sliding window is frame 7 to 11, the third position of the sliding window is frame 13 to 17 and so on.

An overlapping sliding window may overlap by one or more frames. As an example, in a first embodiment a sliding window may be applied which includes 5 frames and which overlaps by 4 frames, i.e. the first position of the sliding window is frame 1 to frame 5, the second position frame 2 to frame 6, the third position frame 3 to frame 7 and so on. In a second embodiment, a sliding window may be applied which includes 5 frames and which overlaps by 1 frame, i.e. the first position of the sliding window covers frame 1 to frame 5, the second position frame 4 to frame 8, the third position frame 7 to frame 11 and so on.

In a preferred embodiment, the sliding rate of the sliding window and frame rate of the input endoscopic video are identical.

For each position of the sliding window, one or more visual features from said frames within the sliding window are extracted and a time image, i.e. the two-dimensional representation of the visual features extracted from the sequence of frames covered by the sliding window at each position, is generated. In a preferred embodiment, more than one visual feature is extracted.

Visual features are those features by which the trained classifier of step 140 identifies the one and more anatomical feature(s) and/or one and more anatomical landmark(s) of interest.

For feature extraction, different families of algorithms, namely local features, global features and deep features, may be employed. For local features, suitable feature descriptors include Scale-Invariant Feature Transform (SIFT), Maximally Stable Extremal Regions (MSER), Features From Accelerated Segment Test (FAST), Speeded Up Robust Features (SURF), Center Surround Extremas (CENSURE), Binary Robust Invariant Scalable Key-points (BRISK) and Fast Retina Key-point (FREAK).

For global features, suitable feature descriptors include Color and Edge Directivity Descriptor (CEDD), Joint Composite Descriptor (JCD), Auto Color-Correlogram, Color-Layout, Edge-Histogram, Rotation Invariant Local Binary Patterns, (Pyramid of) Histograms of Orientation Gradients and Tamura. The advantage with using local and global features are that they are easy and fast to calculate.

Deep features are extracted through deep neural networks (DNN), e.g. convolutional deep neural networks. DNNs are machine learning based neural networks with multiple hidden layers of learned features or variables between the input layer and the output layer.

In one embodiment, supervised methods are used for the DNN to extract the visual features. In a preferred embodiment, unsupervised methods are used for the DNN to extract the visual features, such as variational autoencoders or generative adversarial networks.

In one embodiment, for visual feature extraction, local features and global features are employed. In another embodiment, local features and deep features are employed. In a third embodiment, global and deep features are employed. In a fourth embodiment, local features, global features and deep features are employed.

In another embodiment, a feature buffer (not shown) is added prior step 140 that caches computed features from previous positions of the sliding window for reuse when the window slides to a new position/set of frames. The addition of such a feature buffer avoids recomputing features multiple times, improves throughput and contributes to decrease computation time.

At step 140, a trained classifier is applied to each time image for performing (multi-class) classification, wherein the trained classifier determines the detection scores that indicate the likelihoods that the respective time image contains one or more of said anatomical structures and/or that the respective time image contains one or more of said anatomical landmarks.

In one embodiment, the trained classifier is a DNN adapted for analyzing images or a capsule network adapted for analyzing images and trained to identify said anatomical structures and/or landmarks.

The DNN is trained using methods known in the art. In one embodiment, for the trained classifier in step c)/step 140, a dataset of time images having ground truth labels associated with the one or more anatomical structures and/or one or more anatomical landmarks may be used for training and testing. Any suitable approach can be used to divide the time image dataset. For example, a randomly selected half of the time image dataset can be used for training the DNN and the remaining half of the time image dataset can be used to test the DNN. In another preferred embodiment, the decision layer of the network is used to compute its performance and learn a threshold of detection score for classification using cross-validation.

The resolution of the time image of step 140 may be changed prior to being fed into the classifier. By way of example, time images may initially be fed into the classifier with a lower resolution (than their actual resolution) and provided to the classifier at a higher resolution if the classifier identifies an anatomical structure and/or anatomical landmark of interest. Alternatively, the classifier may process time images of a lower resolution (e.g. disregard features and/or frames) and process time images of a higher resolution when a change of feature values indicate that there are anatomical structure and/or anatomical landmark of interest.

In a preferred embodiment, steps 120 and 140 are carried out in parallel in real-time. In another preferred embodiment, the frame rate of the sequence of frames received in step 100 is at least 30 frames/second and steps 120 and 140 are carried out in parallel in real-time.

Each detection score is compared to a detection threshold learned by the trained classifier during said training. In step 160, in response to the determination that a detection score for a class in the time image is higher than the learned detection threshold, the classification of the time image by the trained classifier is output in real-time.

In one embodiment, a detection signal is output in real-time to the practitioner. The detection signal may be in the form of a visual alert, e.g. displaying an indication of the one or more anatomical structure and/or one or more anatomical landmark on a display. For instance, a label can be used to indicate the presence and/or the location of the anatomical structure and/or landmark, either by overlaying the endoscopic video or separately from the endoscopic video, e.g. below it or next to it. The label can be in the form of a color code, a text, a sign or a shape. Alternatively, the detection signal may be in the form of an audio alert. In another embodiment, a visual and audio alert may be combined. By way of example, an audio alert can indicate the presence of a polyp in the colon while the presence of stool is indicated by a visual alert such as a color-coding in the endoscopic video. The output may also include the detection score(s) for the detected one or more anatomical structures and/or landmarks. In another embodiment, the output may further include instructions or recommendations to the practitioner for adapting the procedure, such as repeating imaging of or zooming in on a particular anatomical location, or further examining a previous anatomical location.

In one embodiment, the classification results are stored on a memory or storage of a computer system, e.g. if the endoscopic video is from a capsule endoscopy where the capsule's motion cannot be controlled.

In yet another embodiment, a detection signal is output in real-time to the practitioner and the classification results are stored on a memory or storage of a computer system. This allows the practitioner to re-view and assess the stored information after the endoscopic procedure has been finalized and to e.g. copy in or transfer images with identified anatomical structures such as polyps into the patient's record.

Figure 2:
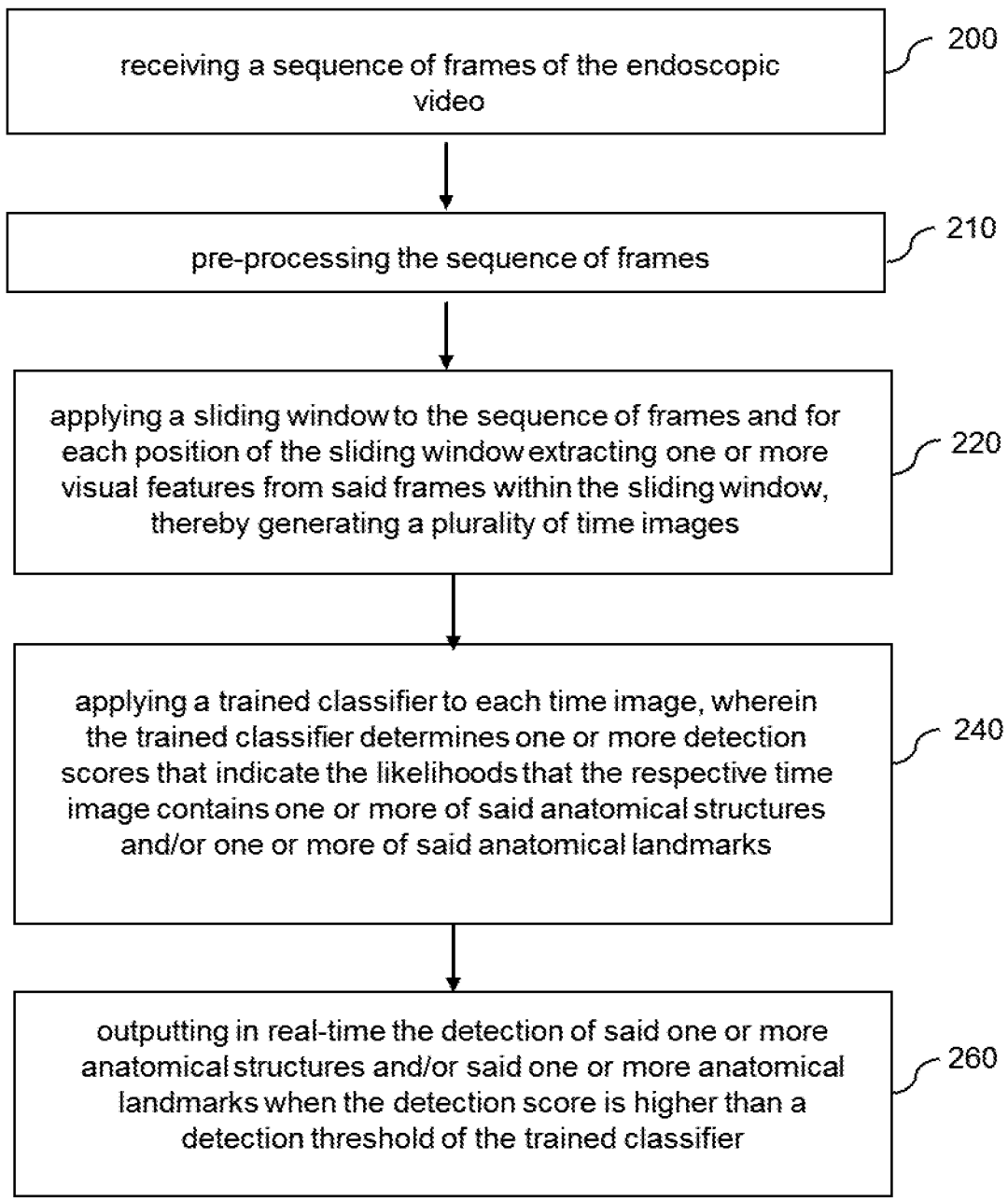
FIG. 2 is another flowchart setting forth steps of a method in accordance with aspects of the present invention.

FIG. 2 is another flowchart setting forth steps of a method in accordance with aspects of the present invention. In some embodiments, the method may be carried out using the system 400 as described with respect to FIG. 4.

The steps 200, 220, 240 and 260 correspond to the steps 100, 120, 140 and 160 described in the context of FIG. 1. However, the method illustrated in FIG. 2 comprises further one or more pre-processing steps 210 prior to step 220, i.e. the frames are pre-processed prior to be processed in accordance with step 220.

Typical pre-processing steps include noise removal, removal of black borders, cropping, resizing, i.e. resizing a frame to obtain the correct size for the feature extraction of step c) such as resizing to 1024×768 pixels, 512×512 pixels or to 256×256 pixels, blurring the edges or removal of metadata.

Metadata in the context of endoscopic procedures include (i) procedure-related information, e.g. equipment manufacturer, type of equipment, serial number, date of procedure, (ii) patient information, e.g. name, gender, birth date, age, type of insurance and (iii) navigational guidance information for practitioner, i.e. the position/location of the endoscope in the anatomical structure under inspection.

Figures 3A, 3B:
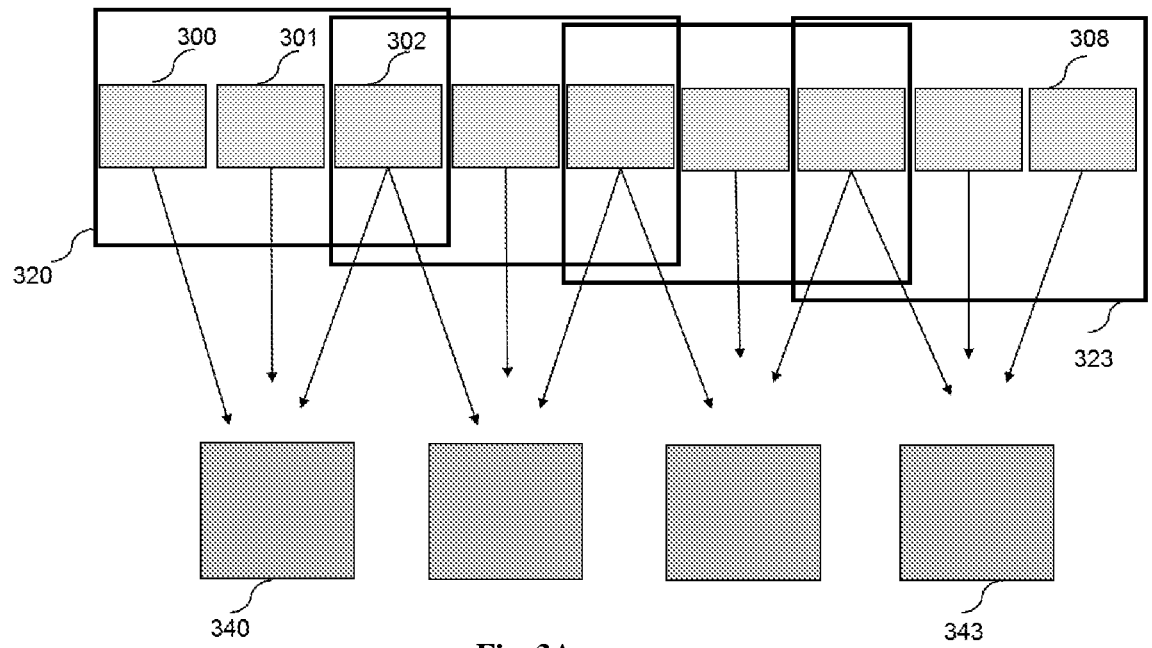
FIG. 3A is an illustration of step b) of a method in accordance with aspects of the invention.
FIG. 3B is an illustration of a time image.

FIG. 3A is an illustration of step b), e.g. step 120 of FIG. 1 or step 220 of FIG. 2, of a method in accordance with aspects of the invention. FIG. 3A illustrates a sequence of frames comprising 9 frames, starting with frame 300 and ending with frame 308. A fixed-size sliding window is applied to this sequence of frames, the sliding window includes 3 frames and it overlaps by 1 frame. Thus at its first position 320, the sliding window includes frames 300, 301 and 302, at its second position, the sliding window includes frames 302, 303 and 304 (the numbers of the latter are not shown in FIG. 3A) etc., and at its fourth position 323, the sliding window includes frames 306, 307 (the numbers of the former are not shown in FIG. 3A) and 308. One or more, preferably more than one, visual features are extracted (depicted by the arrows in the drawing) from frames within the sliding window for each of its positions and time images 340 to 343 are generated, one for each position of the sliding window.

FIG. 3B depicts one of the time images of FIG. 3A, time image 340, in more detail. As mentioned earlier, a time image is the two-dimensional representation of the one or more visual features extracted from the sequence of frames covered by a sliding window at a certain position. Here, it is the two-dimensional representation of the visual features 1 to n, extracted from the sequence of frames including frames 300, 301 and 302 covered by the sliding window at its first position 320. For each frame and feature, the feature value(s) are depicted. By way of example, feature 1 may be color expressed by the RGB color model as a triplet of numerical values for red, green and blue with each component varying from zero to a defined maximum value, e.g. 255. Feature 2 may be the age of the patient, i.e. information contained in the metadata and displayed on each frame. As such, the feature value for feature 2 will be the same for each frame.

Figure 4:
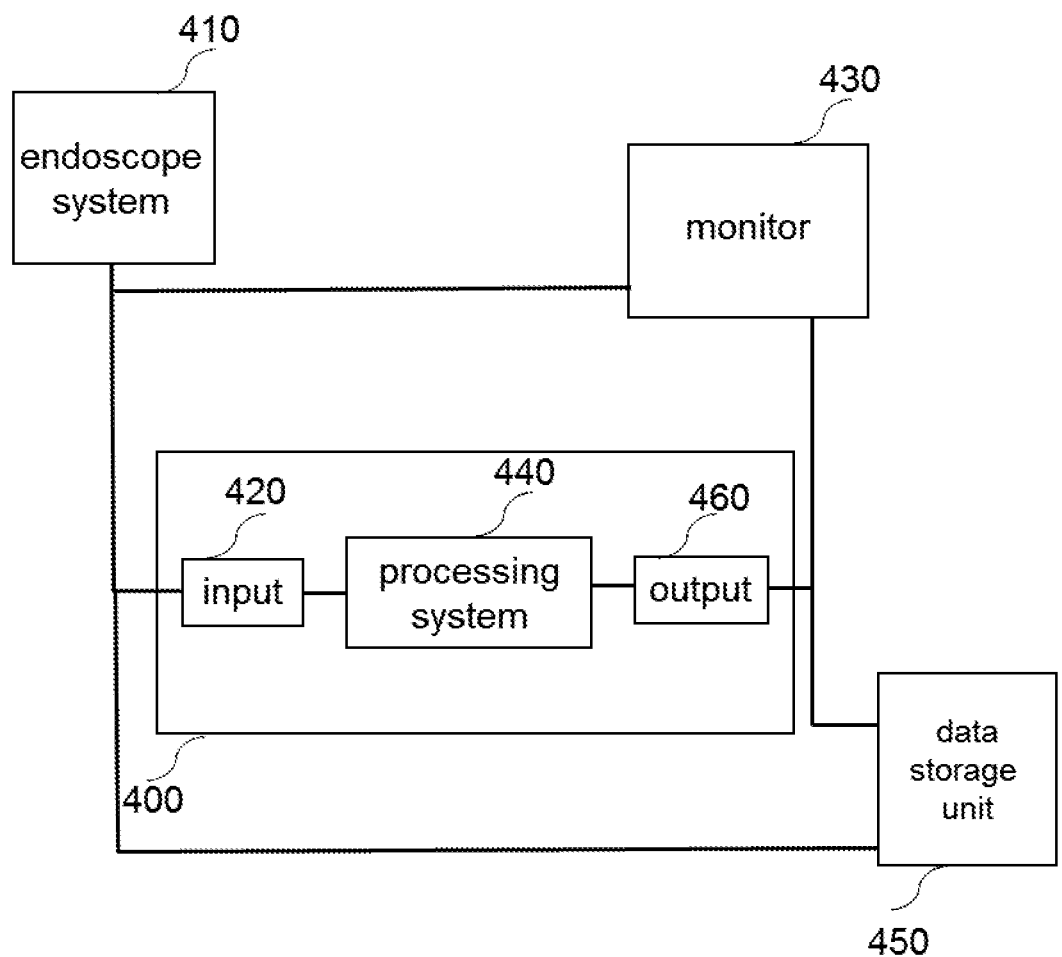
FIG. 4 is a schematic illustration of a system in accordance with aspects of the invention.

Turning now to FIG. 4, a schematic illustration of a system in accordance with aspects of the invention is shown. The system 400 for real-time detection of one or more anatomical structures and/or one or more anatomical landmarks in an endoscopic video comprises an input 420, a processing system 440 and an output 460. In one embodiment, the system is configured for real-time processing. In another embodiment, the system is configured to receive and process at least about 24 frames per second, e.g. 24 frames/s.

The input 420 is configured to receive a sequence of frames of an endoscopic video. It is connected to or in communication, e.g. wireless communication, with the endoscope system 410. In general, suitable inputs are any which allow receiving the video data acquired by the endoscope's video camera in real-time and include USB or micro-USB ports, HDMI ports, an Ethernet or WIFI connection, and other inputs for receiving video data or signals.

The endoscopic video is acquired by an endoscope equipped with a video recording device which is a part of the endoscope system 410. Typically, the endoscope system 410 comprises several components, including an endoscope, i.e. a rigid or flexible tube for insertion into the body, one or more light sources to illuminate the part or region of the body under examination, a video recording device, e.g. a CCD camera or fiber optic camera, for acquiring a video of the part or region of the body under examination, a camera control unit and a monitor 430 for displaying the video in real-time to the practitioner carrying out the endoscopic procedure. The endoscope system may further include a data storage unit, e.g. data storage unit 450, for storing the video data. The endoscope may further include one or more channels for air, suction, administration of medication, contrast agents, dyes or optical imaging agents or for allowing the insertion of medical instruments for manipulating the part or region of the body under examination, e.g. for taking biopsies or the removal of polyps or lesions. In one embodiment, the endoscope may be in the form of a swallowable device capable of acquiring a video of e.g. the GI tract as it passes through the body. The endoscope system can include any type of endoscope suitable for the endoscopic procedures mentioned in this application.

The endoscope system may further include a positioning system configured to monitor the position of an endoscope tip or a swallowable device (e.g. a capsule) and reporting its position to the practitioner.

In one embodiment, the video feed acquired by the endoscope and the information on the position of the endoscope monitored by the positioning system are displayed together on the monitor 430 in real time to the practitioner.

The processing system 440 is configured to access the sequence of frames received and process said sequence of frames with the steps a) to d) as described in detail in this application. The processing system may include one or more CPUs, GPUs and the like.

The output 460 is configured to output in real-time the detection of one or more anatomical structures and/or one or more anatomical landmarks. In general, suitable outputs are any that allow outputting the detection of the anatomical structures and/or landmarks in real-time. Such outputs 460 include one or more electronic connections or means for wireless connection configured for the transmission of data indicative of the detection. The data may be transmitted to a display, e.g. to monitor 430 for providing a visual signal of such detection. In another embodiment, the data may be transmitted to a speaker for providing an audio signal of such detection (not shown). Alternatively or in addition to such a visual and/or audio signal, the data indicative of the detection may be transmitted to a data storage unit, e.g. to data storage unit 450, as shown in FIG. 4, or another data storage unit, e.g. a remote data storage unit (not shown) comprising a database suitable for storing such data or a medical record.

The system 400 may operate autonomously or semi-autonomously, or may receive instructions from a user or a source such as a computer, device or server.

The system 400 is typically a computing device that may comprise other standard components such as memory units, storage or storage devices, graphics hardware, communication interfaces, display controllers, input and output devices (other than input 420 and output 460) and computer software.

An example of such computer software is overlay software that enables the system to overlay the output of step d) over the video acquired by the endo scope, such that an overlaid video is shown on monitor 430 to the practitioner carrying out the endoscopic procedure. Thus, the overlaid video may comprise an annotated sequence of frames in the form of a visual detection signal indicative of e.g. a polyp.

Another example of such computer software is fail-safe software, i.e. software ensuring that the video feed acquired by the endoscope—and the information on the position of the endoscope monitored by the positioning system, if present—are displayed on monitor 430 in real-time to the practitioner carrying out the endoscopic procedure even if the system of the invention (e.g. the system 400) fails.

In another embodiment, such a fail-safe may be implemented as a hardware component present in the computing device. In one embodiment, such hardware component is a video compositor, i.e. a memory buffer comprised in the graphics hardware of the system 400. The video compositor preferably operates independently from the processing system 440, ensuring that the video feed acquired by the endoscope—and the information on the position of the endoscope monitored by the positioning system, if present— is displayed on monitor 430 in real-time to the practitioner carrying out the endoscopic procedure even if the system of the invention (e.g. the system 400) fails. In one embodiment, the video compositor is implemented on a field-programmable gate array.

While the system of the invention allows for real-time detection of one or more anatomical structures and/or one or more anatomical landmarks while the endoscopic video is still being received, it will nevertheless be appreciated that while the detection is real-time, it is not necessarily instantaneous and that there may be processing delays/latencies, of a few milliseconds, e.g. more than 10, 20, 30 or 40 ms or even more than 100 ms.

In one embodiment, the latency is addressed by the video compositor overlaying the results of the processing over the most recent frames of the endoscopic video feed. This leads to a few frames misalignment between the processing and the endoscopic video feed, which is usually acceptable but may lead to mismatches if there is very fast movement in the endoscopic video feed.

Thus, in another embodiment, the video compositor buffers the endoscopic video feed until the processing system 440 has processed the received sequence of frames with the steps a) to d) before overlaying the results of said processing over the endoscopic video feed. This may lead to a latency of more than 100 ms, e.g. 150 ms or 200 ms, but ensures that the overlay matches in a situation where there is very fast movement in the endoscopic video.

In yet another embodiment, the video compositor is configured to either buffer or overlay the results over the most recent frames, i.e. configured to work in either of the two modes described above. In yet another embodiment, the system of the invention is adapted to select the mode the video compositor is working based on the type of information that is to be presented to the practitioner.

The computing device can be a general-purpose device or a special purpose device such as a client, a server, etc. For example, the computing device can be implemented as a personal computer, a tablet computing device, a personal data assistant (PDA), a multimedia terminal, or a mobile telephone.

The processing system 440 may control the overall operation of the computing device by executing computer readable instructions, i.e. the computer program, which define such operation. The computer readable instructions may be stored on a computer readable medium and loaded into a memory when execution of the computer readable instructions is desired. Thus, in one embodiment, the steps a) to d) of the method of the invention are defined by the computer readable instructions stored on the computer readable medium and/or memory and controlled by the processing system 440 executing the computer readable instructions.

In one embodiment, the computer readable medium is a transitory medium, including any signals on networks, in wires, conductors, optical fibers, circuits, etc. In another embodiment, the computer readable medium is a non-transitory medium, including magnetic media such as hard disks, floppy disks, optical media such as CDs, DVDs, semiconductor media such as flash memories and the like.

In one embodiment, the computer readable medium is a transitory medium, including any signals on networks, in wires, conductors, optical fibers, circuits, etc. In another embodiment, the computer readable medium is a non-transitory medium, including magnetic media such as hard disks, floppy disks, optical media such as CDs, DVDs, semiconductor media such as flash memories and the like.

In one embodiment, the system 400 is physically connected to the endoscope system 410 and/or the monitor 430. In another embodiment, the system 400 communicates wirelessly through a network with the endoscope system 410 and/or the monitor 430. The system of the invention 400 may be located remotely from the endoscope system and/or the monitor, and the system may perform steps a) to d) as part of a server or cloud-based service. The system may also include one or more network interfaces for communicating with other devices via a network, such other devices include a display, a speaker or a computing device comprising a database comprising medical records. In one embodiment, the system 400 is a part of the endoscope system 410.

It is apparent to the skilled in the art that the method of the invention is not limited to endoscopic videos, but can be used for the real-time detection of objects, structures and/or patterns in any type of video.

Thus, the method of the invention can be used for the real-time detection of objects, structures and/or patterns in videos obtained from private or public surveillance cameras. An example is the use for facial classification, e.g. for identification of wanted criminals in smart cities or black-listed or restricted persons at schools, hospitals or in private companies. Another example is the detection of unattended baggage on airports, train- or subway stations.

Further, the method of the invention can be used for the real-time detection of objects, structures and/or patterns in videos obtained from satellites or drones. An example is the use for early detection of natural disasters, such as wildfires, floods and volcanic eruptions. Another example is the detection of sharks in proximity to beaches, e.g. by helping to detect sharks in water with low visibility and to distinguish them from other objects of similar size, shape and color, e.g. seals or even to distinguish a harmless shark (e.g. a plankton-eating shark) from a shark which can be potentially dangerous to swimmers and surfers.

The method of the invention can also be used in aquaculture, e.g. fish farming, where videos surveillance of fish in fish cages or ponds is used to assess the activity level of the fish. Typically, fish that display low activity, e.g. swim slowly, do not feed and fish feed needs to be added to obtain the desired growth rates and weight. As of today, an operator watches the video and determines fish activity, but with the method of the invention, the determination of activity levels, their assessment and also subsequent actions as a result of the assessment, e.g. the addition of fish feed, can be automatized.

The method of the invention can also be used for quality control purposes. Today, quality controls are often still carried out manually, e.g. by workers at an assembly line. The method of the invention may be used to detect structures or patters indicative of damaged or sub-standard quality goods on a video obtained from the goods on the assembly line.

Hence, in a fifth aspect, the invention provides a method for real-time detection of one or more objects and/or one or more structures and/or one or more patterns in a video, the method comprising
  a) receiving a sequence of frames of the video;
  b) applying a sliding window to the sequence of frames and for each position of the sliding window extracting one or more visual features from said frames within the sliding window, thereby generating a plurality of time images;
  c) applying a trained classifier to each time image, wherein the trained classifier determines one or more detection scores that indicate the likelihoods that the respective time image contains said one or more objects and/or one or more structures and/or one or more patterns; and
  d) outputting in real-time the detection of said one or more objects and/or one or more structures and/or one or more patterns when the detection score is higher than a detection threshold of the trained classifier.

The one and more objects may be any object of interest, including biological organisms such as humans or animals or parts thereof, articles, items and so on. The one and more structures, i.e. the arrangement and organization of interrelated elements in an object, may be any type of structure of interest, including buildings or non-building structures such as highways, bridges and the like. The one and more patterns may be any kind of pattern of interest, including patterns in nature such as meanders, waves, dunes, cracks or social behavioral patterns of humans and animals.

In a sixth aspect, the invention provides a system for real-time detection of one or more objects and/or one or more structures and/or one or more patterns in a video, said system comprises (i) an input configured to receive a sequence of frames of a video, (ii) a processing system configured to access and process the sequence of frames and (iii) an output configured to output in real-time the detection of said one or more objects and/or one or more structures and/or one or more patterns, wherein the processing system is configured to process the sequence of frames with the steps comprising:

a) receiving a sequence of frames of the video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains said one or more objects and/or one or more structures and/or one or more patterns; and
d) outputting in real-time the detection of said one or more objects and/or one or more structures and/or one or more patterns when the detection score is higher than a detection threshold of the trained classifier.

In a seventh another aspect, the invention provides a computer readable medium storing computer readable instructions for real-time detection of one or more objects and/or one or more structures and/or one or more patterns in a video, the computer program instructions, when executed by a processing system, perform operations comprising:

a) receiving a sequence of frames of the video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains said one or more objects and/or one or more structures and/or one or more patterns; and
d) outputting in real-time the detection of said one or more objects and/or one or more structures and/or one or more patterns when the detection score is higher than a detection threshold of the trained classifier.

In one embodiment, the computer readable medium is a non-transitory computer readable medium. In another embodiment, the computer readable medium is a transitory computer readable medium.

The invention is illustrated in the following non-limiting example:

EXAMPLE 1

Methods 1, 2 and 3 were developed and used for polyp detection in videos from colonoscopy procedures. Method 1/model 1 includes a trained baseline network which was chosen because it is a known high performing classification network capable of classifying images in real-time. Method 2/model 2 includes the extraction of one deep feature for the generation of time images while method 3/model 3 includes the extraction of three visual features, two global features and one deep feature for the generation of time images. Methods 2 and 3 are methods according to the invention.

Figure 5:
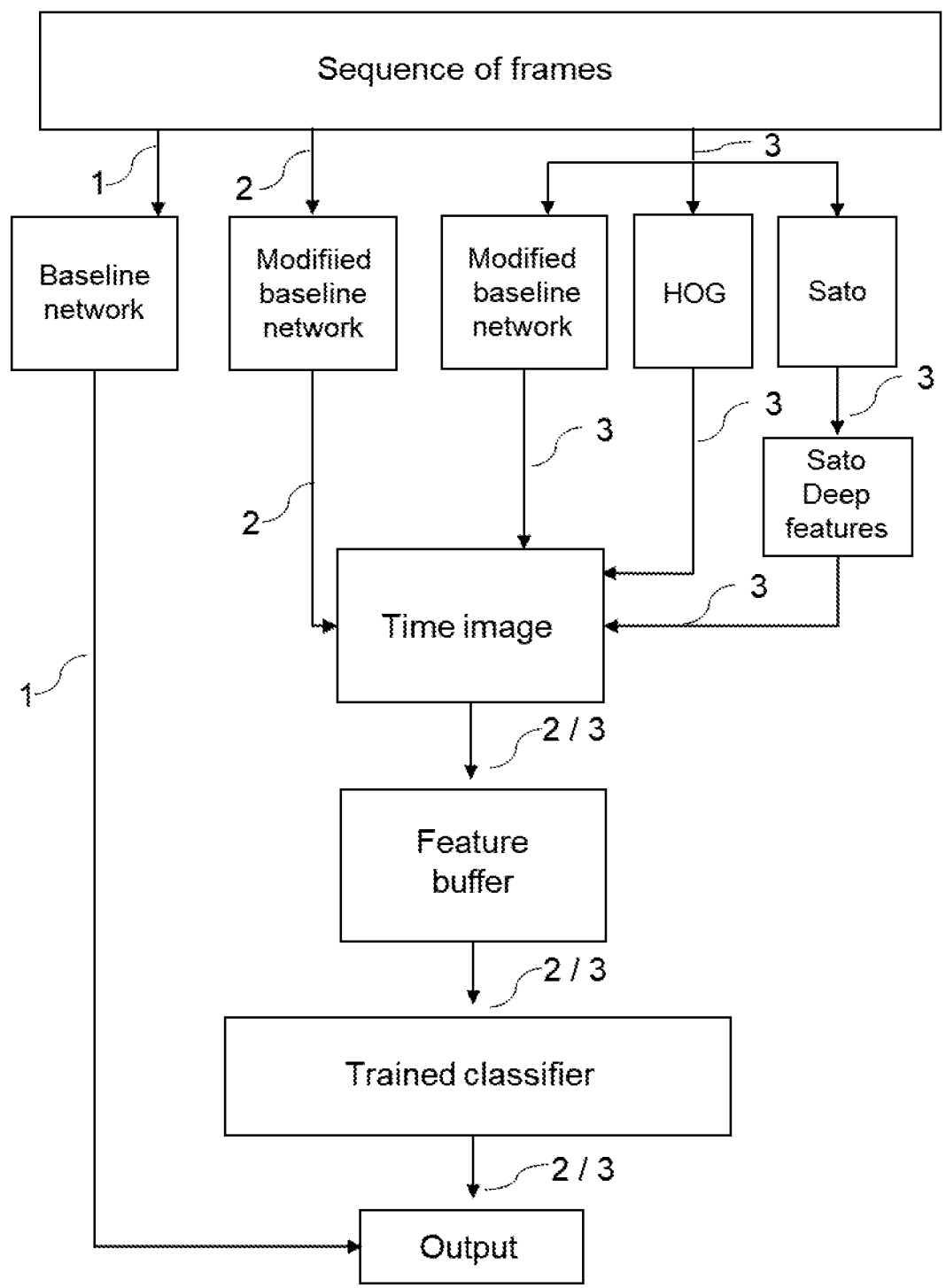
FIG. 5 is an illustration of Example 1.

Certain details of Example 1 are shown in FIG. 5.

Setup

All models were trained on a Nvidia DGX-2 system using Python 3.7, Pytortch 1.5 and Torchvision 0.6. We used an EfficientNet classifier from timm 0.1.26 together with OpenCV 4 and scikit-image 0.17. Inference (i.e. the use of the models for polyp detection) was performed on a commercially available, consumer grade desktop machine with the following specifications: GeForce GTX 1080 Ti, Core i7-7800X at 3.5 GHz and 16 GB memory.

Implementation Details

Training, Validation and Test Data Set:

Videos in full HD quality from 637 colonoscopy procedures (i.e. 637 patients) were collected and polyps were annotated by the physicians performing the procedure. A total of 673 polyps were identified. For each polyp, only the first 250 frames on which such polyp was visible were labeled as positive video frames. For negative video frames, frames without any polyp annotations were randomly selected from patients under the age of 45. Patients of this age group generally have a very low probability of having polyps and the selection of such frames minimizes the risk to include frames in the group of negative video frames on which the physician has failed to detect a polyp. The number of negative video frames to positive video frames (i.e. the class balance) included into the models was 2:1. The video frames were cropped to 1380×1080 pixels to remove the scope guide and metadata such as date of the procedure and the like. Approximately 60% of the data set was used to train the models, 20% to validate the models 20% to test them.

Sliding Window:

A sliding window including 12 frames which was moved by one frame (i.e. overlapping by 11 frames) was applied to the sequence of frames from the test data set. 5 frames within the sliding window were used for the visual feature extraction in a fixed pattern: with the current position of the sliding window including frames 0 (start frame) to 11 (end frame), the start and end frame and the second (frame number 1), the fourth (frame number 3) and the seventh frame (frame number 6) are selected. By moving into the first future position, the sliding window includes frames—1 (start frame) to 10 (end frame). Again, the start and end frame and the second (frame number 0), the fourth (frame number 2), and the seventh frame (frame number 5) are selected and so on for each next future position.

Method 1/Model 1 (this Method is Shown in FIG. 5, (1))

For a reference, a baseline network based on an EfficientNet B3 network was used (M. Tan et al., Proceedings of the 36th International Conference on Machine Learning, Long Beach, CA, PMLR 97, 2019). It was chosen because it is a known high performing classification network which is capable of classifying images in real-time. Since the classification is based on images, the temporal correlation of the images in the video is not taken into account. The network downscales the input image to 300×300 pixels resolution, which is standard practice for most classification networks to increase performance. The baseline network was trained using transfer learning, with weights from the ImageNet dataset. First, the final classification layers of the pretrained network were removed and replaced with a linear classifier which has two output classes (polyp and normal). Then all weights were frozen except the weights of the linear classifier and training was started. An early stopping requirement was defined (no improvement of loss on the validation data set for 30 epochs) and once triggered, all weights were unfrozen in the network and training was continued with a lower learning rate. The classification done by the baseline network was compared to methods 2 and 3 below.

Method 2/Model 2 (this Method is Shown in FIG. 5, (2))

To implement and test a method according to the invention which includes the extraction of one deep feature for the generation of time images, a modified baseline network was used to extract a deep feature vector for each frame by which time images were generated as an input for the trained classifier. To obtain the modified baseline network, the final classification layers of the baseline network described above were removed and the output of the final pooling layers were used directly. This creates a 1D feature vector, based on the information available in the network based on the current frame. By using several feature vectors to generate the time image for input to the trained classifier, a temporal context to the convolutional feature data was added.

Method 3/Model 3 (this Method is Shown in FIG. 5, (3))

In addition to making use of the modified baseline network as described for method 2 above, method 3 (a method according to the invention) includes the extraction of two global visual features:

Histogram of Oriented Gradients (HOG): the basis for using HOG to extract features of interest is that it is useful to describe the shape of a polyp into the network without downscaling, i.e. the shape of the polyp is retained. HOG was used with the following parameters: cell size: 128×128, window size: 256×256, block size: 256×256, block stride: 64×64, orientations: 3. The calculation of HOG was done by OpenCV. It was not real-time optimized, but can easily be real-time optimized by methods and in ways known to a person skilled in the art.

The feature Sato (Y. Sato et al., Med Image Anal 2(2), 1998, 143-168) was used to detect capillary structures by extracting the blood vessels structure in a way that allows the trained classifier to learn normal and polyp blood vessel structure. Since the output/the amount of data of Sato is very large, another deep network trained from scratch and based on EfficientNet B0 was used to compress the output prior to generating the time images. The Sato parameters used were sigmas (1, 3, 5, 7, 9)). The calculation of Sato was done by scikit-image. It was not real-time optimized, but can easily be real-time optimized by methods and in ways known to a person skilled in the art.

Feature Buffer:

For methods 2 and 3, to avoid recomputing features multiple times and to improve throughput, a feature buffer was added that caches computed features from previous positions of the sliding window for reuse when the window slides to a new position/set of frames. Features that are older than 12 frames from the current frame are removed from the buffer cache. This results in improved performance of these methods, as the features must only be computed once for each frame. Thus, introducing a temporal context does not significantly increase computation time.

Trained Classifier:

The trained classifier used in methods 2 and 3 is a smaller fully connected network that allows for quicker inference based on the buffered features. The features were concatenated to a 1D vector where the buffered feature for each frame is stacked concurrently, and then the feature vectors for all frames were concatenated. The network itself consists of 5 blocks which each contain a fully connected (linear) layer, a batch-normalization layer, and a ReLU activation layer. In a last step, the results from the previous layer are fed into a linear classification layer with output dimension N, where N is the number of classes.

Results:

|  | MCC | F1 | Precision | Sensitivity | Specificity | Accuracy |
|---|---|---|---|---|---|---|
| Method 1 | 0.587 | .703 | 68.2% | 72.5% | 87.2% | 83.2% |
| Method 2 | 0.619 | .712 | 72.2% | 70.2% | 91.0% | 85.9% |
| Method 3 | 0.643 | .727 | 76.2% | 69.4% | 92.8% | 87.0% |

Discussion:

The dataset which was used for training and testing aimed to replicate the difficult situation of detecting polyps that are not clearly visible in the image frames. This represents polyps that have not been discovered yet by the performing physician. Only the first 250 frames of when a polyp comes into sight of the video endoscope were included for generating the data set, making the classification particularly difficult for both a machine learning network and a trained physician. In typical evaluations comparing performance of classification methods of polyps, clear images are used, wherein the polyps are well visible in the front and center. However, this does not reflect reality. For physicians, detecting polyps that are not clearly visible is challenging, and it are these polyps that are typically missed. Consequently, a system for real-time detection of polyps should be able to detect polyps in such frames. The baseline network which represents a state-of-the-art classification network thus only achieved an accuracy of 83.2%. As expected, this is lower than published evaluations of such networks which have only attempted the detection of polyps that are clear, up and close to the camera.

Since the ratio of normal frames to polyp frames in the data set was 2:1, the results from the various models were compared in regard to their Matthews correlation coefficients (MCC), that take the class imbalance into account (see B. W. Matthews, Biochim Biophys Acta 405, 1975, 442-451). Method 1, the baseline network, achieved an MCC of 0.587. When compared to method 2, which adds temporal information to the baseline network, the MCC score increased to 0.619, demonstrating the increased classification performance by adding the temporal information to the classification. Also, the accuracy increased by 2.7%. When comparing method 3, which included the modified baseline network and the extraction of two global visual features, the MCC increased further to 0.643 and the accuracy increased by 3.8%, compared to the baseline network.

It could thus be demonstrated that the methods according to the invention significantly increased the classification performance for hard-to-detect polyps.

In order to evaluate the real-time performance potential of a system employing the methods of the invention as described above, a test was run on equivalent consumer hardware (GTX 1080ti) to what could be expected for edge computing (i.e. hardware which is part of a colonoscopy system). Here, both an analysis of the time consumed by calculating deep features for each frame and the time taken to calculate HOG and Sato features was performed, including the deep features for Sato. It is clear from these tests that the trained classifier can run in real time, and the performance of the system is primarily dependent on the features chosen and the implementation of their respective calculations. Average execution time for the steps is listed in the table below. All features can be computed in parallel, with the exception of the Sato deep feature, which must be calculated after the Sato feature.

|  | HOG feature | Sato Feature | Sato deep feature | Modified baseline network | Trained classifier |
| --- | --- | --- | --- | --- | --- |
| Execution time | 45.9 ms | 973.3 ms | 13.1 ms | 15.9 ms | 0.7 ms |

The trained classifier itself requires relatively few calculations, and these calculations are processed extremely quickly on an edge GPU, resulting in an inference time of less than 1 ms. Execution time of HOG and Sato should not be considered in terms of real time aspects since their implementation in the method 3 of this example has not been optimized for real-time detection. Further, the HOG and Sato features may be replaced with a multitude of other features requiring less execution time. To conclude, all deep learning networks used in the methods of the invention ran in less than 20 ms per frame, enabling a system of the invention to run in real time on edge hardware at 50 fps or more.

Various embodiments of the methods and systems of the invention are as follows:

Embodiment 1: A method for real-time detection of one or more anatomical structures and/or one or more anatomical landmarks in an endoscopic video, the method comprising
  a) receiving a sequence of frames of the endoscopic video;
  b) applying a sliding window to the sequence of frames and for each position of the sliding window extracting one or more visual features from said frames within the sliding window, thereby generating a plurality of time images;
  c) applying a trained classifier to each time image, wherein the trained classifier determines one or more detection scores that indicate the likelihoods that the respective time image contains one or more of said anatomical structures and/or one or more of said anatomical landmarks; and
  d) outputting in real-time the detection of said one or more anatomical structures and/or said one or more anatomical landmarks when the detection score is higher than a detection threshold of the trained classifier.

Embodiment 2: The method of embodiment 1, wherein the size of the sliding window is fixed or dynamic.

Embodiment 3: The method of embodiments 1 or 2, wherein the sliding window is overlapping or non-overlapping.

Embodiment 4: The method of embodiments 1 to 3, wherein the sliding rate of the sliding window and frame rate of the input endoscopic video are identical.

Embodiment 5: The method of embodiments 1 to 4, wherein the one or more visual features are extracted by employing algorithms for local feature extraction and/or global feature extraction and/or deep feature extraction.

Embodiment 6: The method of embodiments 1 to 4 wherein the visual features are deep features and such deep features are extracted through deep neural networks (DNN).

Embodiment 7: The method of embodiment 6, wherein supervised methods are used for the DNN to extract such deep features.

Embodiment 8: The method of embodiment 6, wherein unsupervised methods are used for the DNN to extract such deep features.

Embodiment 9: The method of embodiments 1 to 8, wherein the classifier is trained for multi-class classification.

Embodiment 10: The method of embodiments 1 to 9, wherein the classifier is a DNN or a capsule network adapted for analyzing images.

Embodiment 11: The method of embodiments 1 to 10, wherein the output is in the form of a detection signal, preferably a visual alert or an audio alert and/or in the form of data stored on a data storage unit.

Embodiment 12: The method of embodiment 11, wherein the output is in the form of a visual alert which is displayed on a monitor Embodiment 13: The method of embodiment 12, wherein the output is in the form of an overlay video, wherein the visual alert is overlaid over the endoscopic video feed and the overlay video is displayed on a monitor.

Embodiment 14: The method of embodiments 1 to 13, further comprising one or more pre-processing steps prior to step b).

Embodiment 15: The method of embodiment 14, wherein said one or more pre-processing steps are selected from the group consisting of noise removal, removal of black borders, cropping, resizing, blurring the edges and removal of metadata.

Embodiment 16: The method of embodiments 1 to 15, wherein the endoscopic video is of the gastrointestinal tract (GI tract).

Embodiment 17: The method of embodiment 16, wherein the endoscopic video is a colonoscopic video.

Embodiment 18: The method of embodiment 17, wherein the one or more anatomical structures are selected from the group consisting of healthy mucosa, stool, colonic fluid, blood vessels, inflamed mucosa, erosions, lesions and polyps.

Embodiment 19: A method for real-time detection of polyps in a colonoscopic video, the method comprising
  a) receiving a sequence of frames of the colonoscopic video;
  b) applying a sliding window to the sequence of frames and for each position of the sliding window extracting one or more visual features from said frames within the sliding window, thereby generating a plurality of time images;
  c) applying a trained classifier to each time image, wherein the trained classifier determines one or more detection scores that indicate the likelihoods that the respective time image contains one or more polyps; and
  d) outputting in real-time the detection of said one or more polyps when the detection score is higher than a detection threshold of the trained classifier.

Embodiment 20: The method of embodiment 19, wherein the output is in the form of a visual alert which is displayed on a monitor Embodiment 21: The method of embodiment 20, wherein the output is in the form of an overlay video, wherein the visual alert is overlaid over the endoscopic video feed and the overlay video is displayed on a monitor.

Embodiment 22: The method of embodiments 19 to 21, further comprising one or more pre-processing steps prior to step b).

Embodiment 23: The method of embodiment 22, wherein said one or more pre-processing steps are selected from the group consisting of noise removal, removal of black borders, cropping, resizing, blurring the edges and removal of metadata.

Embodiment 24: A system for real-time detection of one or more anatomical structures and/or one or more anatomical landmarks in an endoscopic video, said system comprises (i) an input configured to receive a sequence of frames of the endoscopic video, (ii) a processing system configured to access and process the sequence of frames and (iii) an output configured to output in real-time the detection of said one or more anatomical structures and/or one or more anatomical landmarks, wherein the processing system is configured to process the sequence of frames with the steps comprising:
a) receiving a sequence of frames of the endoscopic video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains one or more of said anatomical structures and/or one or more of said anatomical landmarks; and
d) outputting in real-time the detection of said one or more anatomical structures and/or said one or more anatomical landmarks when the detection score is higher than a detection threshold of the trained classifier.

Embodiment 25: The system of embodiment 24, comprising further one or more components of the group consisting of memory units, storage units, storage devices, graphics hardware, communication interfaces, display controllers, input devices, output devices and computer software.

Embodiment 26: The system of embodiment 25, wherein the computer software is video overlay software.

Embodiment 27: The system of embodiments 24 to 26, wherein the size of the sliding window is fixed or dynamic.

Embodiment 28: The system of embodiments 24 to 27, wherein the sliding window is overlapping or non-overlapping.

Embodiment 29: The system of embodiments 24 to 28, wherein the sliding rate of the sliding window and frame rate of the input endoscopic video are identical.

Embodiment 30: The system of embodiments 24 to 29, wherein the one or more visual features are extracted by employing algorithms for local feature extraction and/or global feature extraction and/or deep feature extraction.

Embodiment 31: The system of embodiments 24 to 29 wherein the visual features are deep features and such deep features are extracted through deep neural networks (DNN).

Embodiment 32: The system of embodiment 31, wherein supervised methods are used for the DNN to extract such deep features.

Embodiment 33: The system of embodiment 31, wherein unsupervised methods are used for the DNN to extract such deep features.

Embodiment 34: The system of embodiments 24 to 33, wherein the classifier is trained for multi-class classification.

Embodiment 35: The system of embodiments 24 to 34, wherein the classifier is a DNN or a capsule network adapted for analyzing images.

Embodiment 36: The system of embodiments 24 to 35, wherein the output is in the form of a detection signal, preferably a visual alert or an audio alert and/or in the form of data stored on a data storage unit.

Embodiment 37: The system of embodiment 36, wherein the output is in the form of a visual alert which is displayed on a monitor Embodiment 38: The system of embodiment 37, wherein the output is in the form of an overlay video, wherein the visual alert is overlaid over the endoscopic video feed and the overlay video is displayed on a monitor.

Embodiment 39: The system of embodiments 24 to 38, wherein the steps further comprise one or more pre-processing steps prior to step b).

Embodiment 40: The system of embodiment 39, wherein said one or more pre-processing steps are selected from the group consisting of noise removal, removal of black borders, cropping, resizing, blurring the edges and removal of metadata.

Embodiment 41: The system of embodiments 24 to 40, wherein the endoscopic video is of the gastrointestinal tract (GI tract).

Embodiment 42: The system of embodiment 41, wherein the endoscopic video is a colonoscopic video.

Embodiment 43: The system of embodiment 41, wherein the one or more anatomical structures are selected from the group consisting of healthy mucosa, stool, colonic fluid, blood vessels, inflamed mucosa, erosions, lesions and polyps.

Embodiment 44: A system for real-time detection of polyps in an colonoscopic video, said system comprises (i) an input configured to receive a sequence of frames of the endoscopic video, (ii) a processing system configured to access and process the sequence of frames and (iii) an output configured to output in real-time the detection of said polyps, wherein the processing system is configured to process the sequence of frames with the steps comprising:
a) receiving a sequence of frames of the colonoscopic video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains one or more of polyps; and
d) outputting in real-time the detection of said one or more polyps when the detection score is higher than a detection threshold of the trained classifier.

Embodiment 45: The system of embodiment 44, wherein the output is in the form of a visual alert which is displayed on a monitor Embodiment 46: The system of embodiment 45, wherein the output is in the form of an overlay video, wherein the visual alert is overlaid over the endoscopic video feed and the overlay video is displayed on a monitor.

Embodiment 47: The system of embodiments 44 to 46, wherein said steps further comprise one or more pre-processing steps prior to step b).

Embodiment 48: The system of embodiment 47, wherein said one or more pre-processing steps are selected from the group consisting of noise removal, removal of black borders, cropping, resizing, blurring the edges and removal of metadata.

Embodiment 49: The system of any of embodiments 24 to 48, wherein the system further comprises graphics hardware comprising a video compositor configured to operate independently of the processing system ensuring that the video is displayed on a monitor in real-time, even if the system fails.

Embodiment 50: A computer readable medium storing computer readable instructions for real-time detection of one or more anatomical structures and/or one or more anatomical landmarks in an endoscopic video, the computer program instructions, when executed by a processing system, perform operations comprising:
a) receiving a sequence of frames of the endoscopic video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains one or more of said anatomical structures and/or one or more of said anatomical landmarks; and
d) outputting in real-time the detection of said one or more anatomical structures and/or said one or more anatomical landmarks when the detection score is higher than a detection threshold of the trained classifier.

Embodiment 51: The computer readable medium of embodiment 50, wherein the size of the sliding window is fixed or dynamic.

Embodiment 52: The computer readable medium of embodiments 50 or 51, wherein the sliding window is overlapping or non-overlapping.

Embodiment 53: The computer readable medium of embodiments 50 to 52, wherein the sliding rate of the sliding window and frame rate of the input endoscopic video are identical.

Embodiment 54: The computer readable medium of embodiments 50 to 53, wherein the one or more visual features are extracted by employing algorithms for local feature extraction and/or global feature extraction and/or deep feature extraction.

Embodiment 55: The computer readable medium of embodiments 50 to 53 wherein the visual features are deep features and such deep features are extracted through deep neural networks (DNN).

Embodiment 56: The computer readable medium of embodiment 55, wherein supervised methods are used for the DNN to extract such deep features.

Embodiment 57: The computer readable medium of embodiment 55, wherein unsupervised methods are used for the DNN to extract such deep features.

Embodiment 58: The computer readable medium of embodiments 50 to 57, wherein the classifier is trained for multi-class classification.

Embodiment 59: The computer readable medium of embodiments 50 to 58, wherein the classifier is a DNN or a capsule network adapted for analyzing images.

Embodiment 60: The computer readable medium of embodiments 50 to 59, wherein the output is in the form of a detection signal, preferably a visual alert or an audio alert and/or in the form of data stored on a data storage unit.

Embodiment 61: The computer readable medium of embodiment 60, wherein the output is in the form of a visual alert which is displayed on a monitor.

Embodiment 62: The computer readable medium of embodiment 61, wherein the output is in the form of an overlay video, wherein the visual alert is overlaid over the endoscopic video feed and the overlay video is displayed on a monitor.

Embodiment 63: The computer readable medium of embodiments 50 to 62, wherein said operations comprise one or more pre-processing steps prior to b).

Embodiment 64: The computer readable medium of embodiment 63, wherein said one or more pre-processing steps are selected from the group consisting of noise removal, removal of black borders, cropping, resizing, blurring the edges and removal of metadata.

Embodiment 65: The computer readable medium of embodiments 50 to 64, wherein the endoscopic video is of the gastrointestinal tract (GI tract).

Embodiment 66: The computer readable medium of embodiment 65, wherein the endoscopic video is a colonoscopic video.

Embodiment 67: The computer readable medium of embodiment 65 or 66, wherein the one or more anatomical structures are selected from the group consisting of healthy mucosa, stool, colonic fluid, blood vessels, inflamed mucosa, erosions, lesions and polyps.

Embodiment 68: A computer readable medium storing computer readable instructions for real-time detection of polyps in a colonoscopic video, the computer program instructions, when executed by a processing system, perform operations comprising:
a) receiving a sequence of frames of the colonoscopic video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains one or more polyps; and
d) outputting in real-time the detection of said one or more polyps when the detection score is higher than a detection threshold of the trained classifier.

Embodiment 69: The computer readable medium of embodiment 68, wherein the output is in the form of a visual alert which is displayed on a monitor.

Embodiment 70: The computer readable medium of embodiment 69, wherein the output is in the form of an overlay video, wherein the visual alert is overlaid over the endoscopic video feed and the overlay video is displayed on a monitor.

Embodiment 71: The computer readable medium of embodiments 68 to 70, wherein said operations comprise one or more pre-processing steps prior to b).

Embodiment 72: The computer readable medium of embodiment 71, wherein said one or more pre-processing steps are selected from the group consisting of noise removal, removal of black borders, cropping, resizing, blurring the edges and removal of metadata.

Embodiment 73: A method for real-time detection of one or more objects and/or one or more structures and/or one or more patterns in a video, the method comprising
a) receiving a sequence of frames of the video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains said one or more objects and/or one or more structures and/or one or more patterns; and
d) outputting in real-time the detection of said one or more objects and/or one or more structures and/or one or more patterns when the detection score is higher than a detection threshold of the trained classifier.

Embodiment 74: The method of embodiment 73, wherein the size of the sliding window is fixed or dynamic.

Embodiment 75: The method of embodiments 73 or 74, wherein the sliding window is overlapping or non-overlapping.

Embodiment 76: The method of embodiments 73 to 75, wherein the sliding rate of the sliding window and frame rate of the input video are identical.

Embodiment 77: The method of embodiments 73 to 76, wherein the one or more visual features are extracted by employing algorithms for local feature extraction and/or global feature extraction and/or deep feature extraction.

Embodiment 78: The method of embodiments 73 to 76 wherein the visual features are deep features and such deep features are extracted through deep neural networks (DNN).

Embodiment 79: The method of embodiment 78, wherein supervised methods are used for the DNN to extract such deep features.

Embodiment 80: The method of embodiment 78, wherein unsupervised methods are used for the DNN to extract such deep features.

Embodiment 81: The method of embodiments 73 to 80, wherein the classifier is trained for multi-class classification.

Embodiment 82: The method of embodiments 73 to 81, wherein the classifier is a DNN or a capsule network adapted for analyzing images.

Embodiment 83: The method of embodiments 73 to 82, wherein the output is in the form of a detection signal, preferably a visual alert or an audio alert and/or in the form of data stored on a data storage unit.

Embodiment 84: The method of embodiment 83, wherein the output is in the form of a visual alert which is displayed on a monitor.

Embodiment 85: The method of embodiment 84, wherein the output is in the form of an overlay video, wherein the visual alert is overlaid over the video feed and the overlay video is displayed on a monitor.

Embodiment 86: The method of embodiments 73 to 85, further comprising one or more pre-processing steps prior to step b).

Embodiment 87: The method of embodiment 86, wherein said one or more pre-processing steps are selected from the group consisting of noise removal, removal of borders, cropping, resizing, blurring the edges and removal of metadata.

Embodiment 88: A system for real-time detection of one or more objects and/or one or more structures and/or one or more patterns in a video, said system comprises (i) an input configured to receive a sequence of frames of a video, (ii) a processing system configured to access and process the sequence of frames and (iii) an output configured to output in real-time the detection of said one or more objects and/or one or more structures and/or one or more patterns, wherein the processing system is configured to process the sequence of frames with the steps comprising:
a) receiving a sequence of frames of the video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains said one or more objects and/or one or more structures and/or one or more patterns; and
d) outputting in real-time the detection of said one or more objects and/or one or more structures and/or one or more patterns when the detection score is higher than a detection threshold of the trained classifier.

Embodiment 89: The system of embodiment 88, comprising further one or more components of the group consisting of memory units, storage units, storage devices, graphics hardware, communication interfaces, display controllers, input devices, output devices and computer software.

Embodiment 90: The system of embodiment 89, wherein the computer software is video overlay software.

Embodiment 91: The system of embodiments 88 to 90, wherein the size of the sliding window is fixed or dynamic.

Embodiment 92: The system of embodiments 88 to 91, wherein the sliding window is overlapping or non-overlapping.

Embodiment 93: The system of embodiments 88 to 92, wherein the sliding rate of the sliding window and frame rate of the input video are identical.

Embodiment 94: The system of embodiments 88 to 93, wherein the one or more visual features are extracted by employing algorithms for local feature extraction and/or global feature extraction and/or deep feature extraction.

Embodiment 95: The system of embodiments 88 to 93 wherein the visual features are deep features and such deep features are extracted through deep neural networks (DNN).

Embodiment 96: The system of embodiment 95, wherein supervised methods are used for the DNN to extract such deep features.

Embodiment 97: The system of embodiment 95, wherein unsupervised methods are used for the DNN to extract such deep features.

Embodiment 98: The system of embodiments 88 to 97, wherein the classifier is trained for multi-class classification.

Embodiment 99: The system of embodiments 88 to 98, wherein the classifier is a DNN or a capsule network adapted for analyzing images.

Embodiment 100: The system of embodiments 88 to 99, wherein the output is in the form of a detection signal, preferably a visual alert or an audio alert and/or in the form of data stored on a data storage unit.

Embodiment 101: The system of embodiment 100, wherein the output is in the form of a visual alert which is displayed on a monitor.

Embodiment 102: The system of embodiment 101, wherein the output is in the form of an overlay video, wherein the visual alert is overlaid over the video feed and the overlay video is displayed on a monitor.

Embodiment 103: The system of embodiments 88 to 102, wherein the steps further comprise one or more pre-processing steps prior to step b).

Embodiment 104: The system of embodiment 103, wherein said one or more pre-processing steps are selected from the group consisting of noise removal, removal of black borders, cropping, resizing, blurring the edges and removal of metadata.

Embodiment 105: The system of embodiments 88 to 104, wherein the system is configured to receive and process at least 24 frames per second.

Embodiment 106: The system of any of embodiments 88 to 104, wherein the system further comprises graphics hardware comprising a video compositor configured to operate independently of the processing system ensuring that the video is displayed on a monitor in real-time, even if the system fails.

Embodiment 107: A computer readable medium storing computer readable instructions for real-time detection of one or more objects and/or one or more structures and/or one or more patterns in a video, the computer program instructions, when executed by a processing system, perform operations comprising:
a) receiving a sequence of frames of the video;
b) applying a sliding window to the sequence of frames and for each position of the sliding window extracting one or more visual features from said frames within the sliding window, thereby generating a plurality of time images;
c) applying a trained classifier to each time image, wherein the trained classifier determines one or more detection scores that indicate the likelihoods that the respective time image contains said one or more objects and/or one or more structures and/or one or more patterns; and
d) outputting in real-time the detection of said one or more objects and/or one or more structures and/or one or more patterns when the detection score is higher than a detection threshold of the trained classifier.

Embodiment 108: The computer readable medium of embodiment 107, wherein the size of the sliding window is fixed or dynamic.

Embodiment 109: The computer readable medium of embodiments 107 or 108, wherein the sliding window is overlapping or non-overlapping.

Embodiment 110: The computer readable medium of embodiments 107 to 109, wherein the sliding rate of the sliding window and frame rate of the input video are identical.

Embodiment 111: The computer readable medium of embodiments 107 to 110, wherein the one or more visual features are extracted by employing algorithms for local feature extraction and/or global feature extraction and/or deep feature extraction Embodiment 112: The computer readable medium of embodiments 107 to 110 wherein the visual features are deep features and such deep features are extracted through deep neural networks (DNN).

Embodiment 113: The computer readable medium of embodiment 112, wherein supervised methods are used for the DNN to extract such deep features.

Embodiment 114: The computer readable medium of embodiment 112, wherein unsupervised methods are used for the DNN to extract such deep features.

Embodiment 115: The computer readable medium of embodiments 107 to 114, wherein the classifier is trained for multi-class classification.

Embodiment 116: The computer readable medium of embodiments 107 to 115, wherein the classifier is a DNN or a capsule network adapted for analyzing images.

Embodiment 117: The computer readable medium of embodiments 107 to 116, wherein the output is in the form of a detection signal, preferably a visual alert or an audio alert and/or in the form of data stored on a data storage unit.

Embodiment 118: The computer readable medium of embodiment 117, wherein the output is in the form of a visual alert which is displayed on a monitor.

Embodiment 119: The computer readable medium of embodiment 118, wherein the output is in the form of an overlay video, wherein the visual alert is overlaid over the video feed and the overlay video is displayed on a monitor.

Embodiment 120: The computer readable medium of embodiments 107 to 119, wherein the operations comprise one or more pre-processing steps prior to b).

Embodiment 121: The computer readable medium of embodiment 120 wherein said one or more pre-processing steps are selected from the group consisting of noise removal, removal of black borders, cropping, resizing, blurring the edges and removal of metadata.

Embodiment 122. An endoscope system comprising the system according to any of embodiments 24 to 49 and an endoscope connected to or in communication with the input of said system.

The invention claimed is:

1. A computer-implemented method for real-time detection of polyps in a video from a colonoscopy, the method comprising
a) receiving a sequence of frames of the video from the colonoscopy;
b) applying a sliding window to the sequence of frames over time, and for each time position of the sliding window extracting one or more visual features from a plurality of frames within the sliding window to generate a respective time image, thereby generating a plurality of time images;
c) applying a trained classifier to each time image, wherein the trained classifier determines one or more detection scores that indicate likelihoods that the respective time image contains one or more polyps; and d) outputting in real-time a detection of said one or more polyps when the one or more detection scores are higher than a detection threshold of the trained classifier.

2. The method of claim 1, wherein the size of the sliding window is fixed or dynamic.

3. The method of claim 1, wherein the sliding window is overlapping or non-overlapping.

4. The method of claim 1, wherein a sliding rate of the sliding window and a frame rate of the video from the colonoscopy are identical.

5. The method of claim 1, wherein the one or more visual features are extracted by employing algorithms for local feature extraction and/or global feature extraction and/or deep feature extraction.

6. The method of claim 1, wherein the one or more visual features are deep features and said deep features are extracted through deep neural networks (DNN).

7. The method of claim 1, wherein the classifier is trained for multi-class classification.

8. The method of claim 1, wherein the output is in the form of a detection signal selected from the group consisting of-a visual alert and an audio alert and/or is in the form of data stored on a data storage unit.

9. The method of claim 1, further comprising one or more pre-processing steps prior to step b), wherein said pre-processing steps are selected from the group consisting of noise removal, removal of black borders, cropping, resizing, blurring of edges, and removal of metadata.

10. A system for real-time detection of polyps in a video from a colonoscopy, wherein said system comprises (i) an input configured to receive a sequence of frames of the video from the colonoscopy, (ii) a processing system configured to access and process the sequence of frames and (iii) an output configured to output in real-time a detection of said polyps, wherein the processing system is configured to process the sequence of frames with the steps comprising:
  a) receiving the sequence of frames of the video from the colonoscopy;
  b) applying a sliding window to the sequence of frames over time, and for each time position of the sliding window extracting one or more visual features from said a plurality of frames within the sliding window to generate a respective time image, thereby generating a plurality of time images;
  c) applying a trained classifier to each time image, wherein the trained classifier determines one or more detection scores that indicate likelihoods that the respective time image contains one or more polyps; and
  d) outputting in real-time the detection of said one or more polyps when the one or more detection scores are higher than a detection threshold of the trained classifier.

11. The system of claim 10, wherein the size of the sliding window is fixed or dynamic.

12. The system of claim 10, wherein the sliding window is overlapping or non-overlapping.

13. The system of claim 10, wherein a sliding rate of the sliding window and a frame rate of the input video are identical.

14. The system of claim 10, wherein the one or more visual features are extracted by employing algorithms for local feature extraction and/or global feature extraction and/or deep feature extraction.

15. The system of claim 10, wherein the visual features are deep features and said deep features are extracted through deep neural networks (DNN).

16. The system of claim 10, wherein the classifier is trained for multi-class classification.

17. The system of claim 10, wherein the output is in the form of a detection signal selected from group consisting of a visual alert and an audio alert and/or is in the form of data stored on a data storage unit.

18. The system of claim 17, wherein the output is in the form of a visual alert which is overlaid over a video feed from the colonoscopy to result in an overlay video which is displayed on a monitor.

19. The system of claim 10, wherein the steps further comprise one or more pre-processing steps prior to step b), wherein the one or more pre-processing steps are selected from the group consisting of noise removal, removal of black borders, cropping, resizing, blurring of edges, and removal of metadata.

20. The system of claim 10, wherein the system further comprises graphics hardware comprising a video compositor configured to operate independently of the processing system, ensuring that the video is displayed on a monitor in real-time, even if the system fails.

21. A colonoscope system comprising the system of claim 10 and a colonoscope connected to or in communication with the input of said system.

22. A non-transitory, computer readable medium storing computer readable instructions for real-time detection of polyps in a video from a colonoscopy, wherein the computer program instructions, when executed by a processing system, cause the processing system to perform operations comprising:
  a) receiving a sequence of frames of the video from the colonoscopy;
  b) applying a sliding window to the sequence of frames over time, and for each time position of the sliding window extracting one or more visual features from a plurality of frames within the sliding window to generate a respective time image, thereby generating a plurality of time images;
  c) applying a trained classifier to each time image, wherein the trained classifier determines one or more detection scores that indicate likelihoods that the respective time image contains one or more polyps; and
  d) outputting in real-time the detection of said one or more polyps when the one or more detection scores are higher than a detection threshold of the trained classifier.

* * * * *